Figure 1:
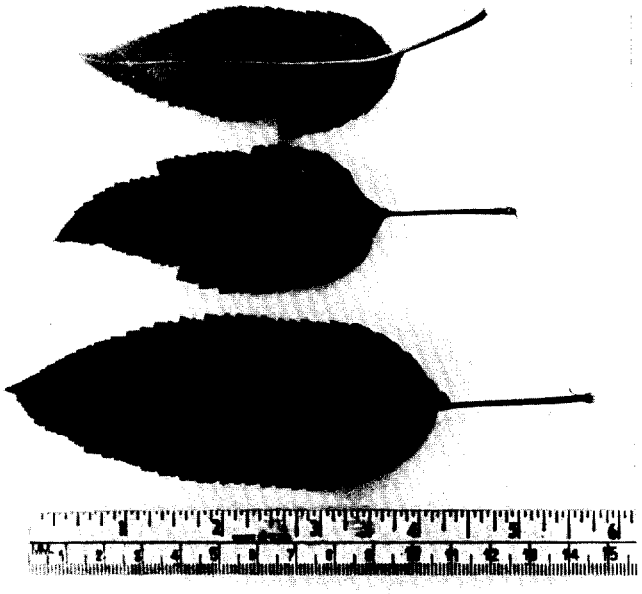
Figure 2:
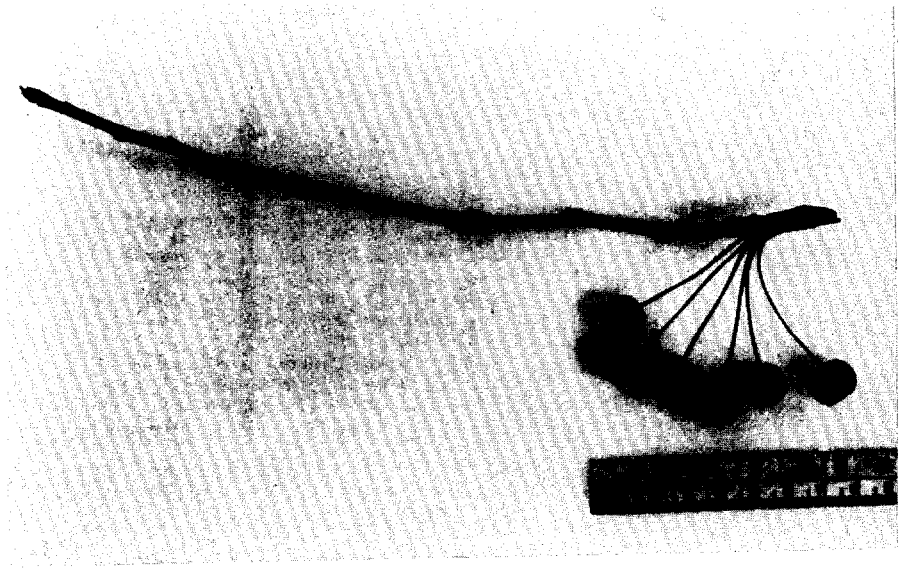
Figure 3:
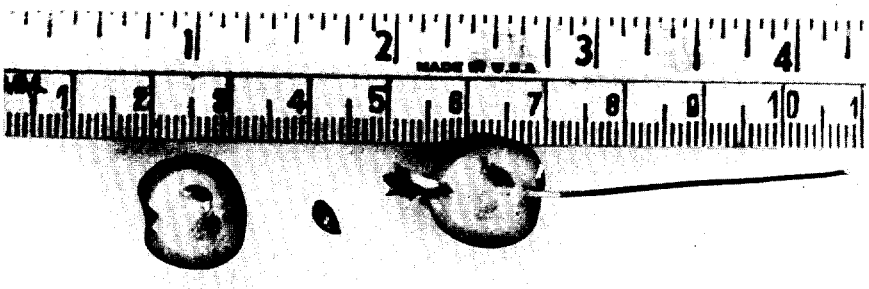
Figure 4:
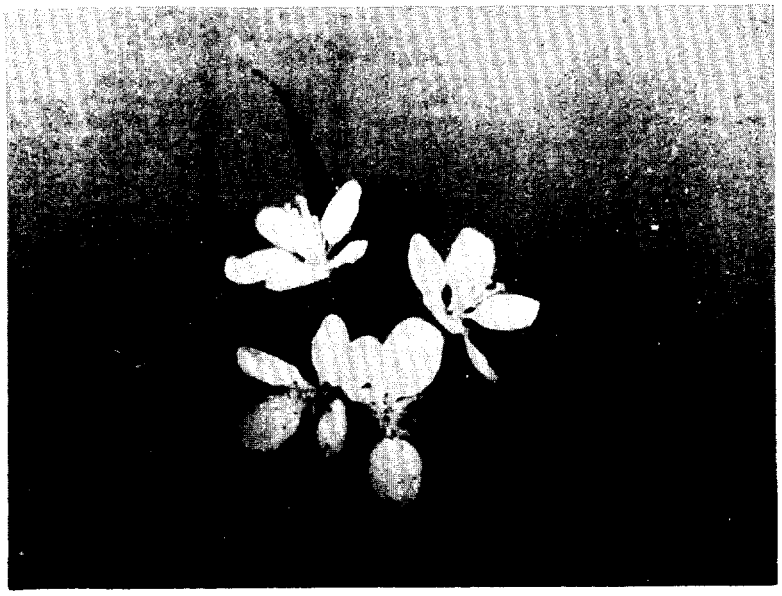
Figure 5:
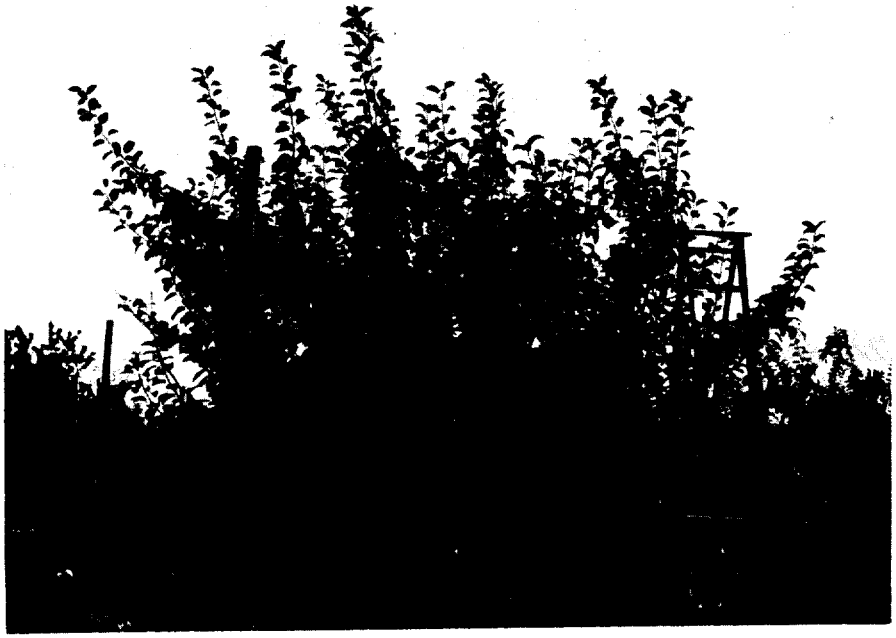

United States Patent [19]

Cummins et al.

[11] Patent Number: Plant 5,333

[45] Date of Patent: Nov. 13, 1984

[54] APPLE TREE

[75] Inventors: James N. Cummins; Herb S. Aldwinckle, both of Geneva, N.Y.; Ross E. Byers, Winchester, Va.

[73] Assignee: Cornell Research Foundation, Inc., Ithaca, N.Y.

[21] Appl. No.: 391,897

[22] Filed: Jun. 24, 1982

[51] Int. Cl.[3] ..... A01H 5/03

[52] U.S. Cl. ..... Plt./34

[58] Field of Search ..... Plt./34

*Primary Examiner*—Robert E. Bagwill

[57] ABSTRACT

An apple tree which is vole-resistant and useful for rootstocks and trunkstocks.

5 Drawing Figures

The present invention relates to a new and distinct cultivar of apple tree Novole which we discovered in a test planting belonging to New York State Agricultural Experiment Station, Cornell University, Geneva, Ontario County, N.Y. This discovery is a product of the apple rootstock breeding program of New York State Agricultural Experiment Station.

In 1963, seeds of *Malus prunifolia* were sent from Morioka research station in Japan to the U.S. Department of Agriculture Plant Introduction Station in Glenn Dale, Md. Eleven seedlings survived; a scion stick of 1 of these was sent to NYSAES and was grafted onto domestic apple seedlings in 1968. We propagated this cultivar asexually by budding, grafting and cuttage. Rigorous testing of this clone in our laboratories, greenhouses, nurseries and orchards revealed that it is resistant to *Erwinia amylovora (fire blight), Phytophthora cactorum* (crown rot), *Venturia inaequalis* (apple scab), *Microtus pinetorum* (pine vole) and *M. pennsylvanicus* (meadow vole), all serious pests of apple trees. This clone is sensitive to apple stem pitting virus and to apple stem grooving virus, but when used as a stock, it is compatible when grafted with virus-free scion cultivars such as 'Delicious' and 'McIntosh'. As a rootstock, this clone supports vigorous growth of the scion cultivar, making a "standard" tree; fruit production by the scion cultivar commences relatively early.

Asexual propagation of this new cultivar by grafting, as we have done in Ontario County, New York, has shown that these attributes are transmitted through succeeding asexual propagations.

The following is a detailed description of our new cultivar Novole. Accompanying photographs depict fruiting habit and fruit characteristics, tree habit and leaf characteristics.

The first photograph shows the leaves of the new variety; at left, typical leaf from near midpoint of shoot; at center and right, leaves from lower nodes, showing partial lobing. Note lack of stipules.

The second photograph shows the fruiting habit of the new variety. Long, slender peduncles with pendant fruit are typical.

The third photograph shows longisections of fruit; left, typical fruit with calyx and external remnants of stamens and pistil absized; center, seed showing typical cordate shape; right, atypical fruit with floral parts retained.

The fourth photograph shows flowers on a leaf-bud cutting (the entire plant is about 5 cm tall). The new variety is very precocious and many axiallary buds are mixed vegetative and flower buds.

The fifth photograph is "Imperial McIntosh" on the new variety (about seven years old). This is a very vigorous tree of "standard" size, but fruiting is heavier and began earlier than on domestic seedling stocks.

The numerical color specifications employed in the following descriptions of shoots, leaves, flowers and fruit are those of The Royal Horticultural Society Colour Chart (1976).

The new variety is further characterized as follows:

TREE

Small, upright-spreading, vigor medium. Winterhardy under conditions at Geneva, N.Y. Very productive, with some tendency toward biennial bearing if not pruned.

SHOOTS

Dark brown (166B to 175A), stiff, usually short (ca. 30 cm). Pubescence is slight. Lenticels are medium in size, raised, tan (165D), few. Axillary buds are sessile; may be either vegetative or mixed vegetative and fruit; most are appressed; bud scales are quite large on mixed buds. Completely free of burrknots and sphaeroblasts.

LEAVES

Lanceolate; margins coarsely serrate, but basipetal 1–4 leaves usually 1- to 3-lobed; apex acute, occasionally acuminate; base abrupt; lamella size averages 10 cm long×4 cm wide, but variable depending on growth rate; lamella flat or slightly waved; stipules very small, usually 1–1.5 mm long, moderately stiff; adaxial lamella surface dull dark green (132A–133A), slightly pubescent; adaxial lamella surface light green (136C–D), lightly pubescent. Spring budbreak midseason; autumn leaffall moderately early, with variable yellow but without red leaf coloration.

FLOWERS

Single, very numerous, typically 7 but as many as 12 per truss. At full balloon stage, bud is pale rose (49C fading through 49D); the 5 petals are white (155D) after opening. Flowers average about 30 mm ±5 diameter. Pollen is yellow-orange (15A), very abundant, germinates rapidly, and is long-lived in refrigerated storage. In a given truss, individual flowers open over a period of 3–6 days. Bloom period usually begins with 'Delicious' and lasts 7–10 days.

FRUIT

Round, symmetrical, with no calyx or residual stamens or pistils; rare fruits with retained calyxes are round-conic to conic. Fruits are about 10 mm diameter × 10 mm long. Cavity medium in depth and breadth, regular. Peduncle long, 4–6 cm, slender, moderately pubescent, fruit pendant. Calyx usually dehiscent, basin medium, obtuse, regular. Lenticels on fruit rare, very small, raised, rough, round, gray. Core distant, very large. Core line perpendicular to basin, not meeting at cavity. Carpels axile, 5 in number, occasionally tufted, cordate. Seeds small, 4 mm long × 2 mm; up to 3 per carpel, usually 2; acute to acuminate; light brown. Flesh yellow-orange (23C), lighter outside core line; firm; coarse; acid. Skin color orange (25C) to orange-red (30D); bloom heavy.

When grafted as a rootstock with virus-free scion cultivars such as 'Delicious' and 'McIntosh', 'Novole' supports vigorous growth of the scion cultivar, making a "standard" tree; fruit production by the scion cultivar commences relatively early.

Asexual propagation of this new cultivar by grafting, as we have done in Ontario County, New York, has shown that these attributes are transmitted through succeeding asexual propagations.

'Novole' is further characterized as:

Resistant to fire blight, crown rot, apple scab, pine vole and meadow vole. Sensitive to apple stem pitting and apple stem grooving virus. Susceptible to wooly apple aphids, European red mite and whiteflies.

USEFULNESS (1) As a vigorous rootstock resistant to voles and crown rot; (2) As an ornamental crabapple resistant to voles, crown rot, apple scab and fire blight; (3) As a pollinizer for use in commercial apple orchards.

We claim:

1. A new and distinct cultivar of apple tree, substantially as shown and described herein, characterized particularly as to novelty by being resistant to pine voles, meadow voles, and crown rot and being easily propagated by cuttage.

* * * * *